United States Patent [19]

Khromov-Borisov et al.

[11] 4,137,239
[45] Jan. 30, 1979

[54] p,p,"BIS-QUATERNARY AMMONIUM SALTS OF p-TERPHENYL AND METHOD OF PREPARING SAME

[76] Inventors: Nikolai V. Khromov-Borisov, ulitsa Nalichnaya, 36, korpus 9, kv. 214; Samuil F. Torf, ulitsa Kurchatova, 4, kv. 86; Valentina P. Cherepanova, 4 linia, 19, kv. 5; Anatoly F. Danilov, V.O. 9 linia, 54, kv. 36, all of Leningrad, U.S.S.R.

[21] Appl. No.: 689,979

[22] Filed: May 26, 1976

[51] Int. Cl.$^2$ .................... C07D 403/10; C07C 87/68; A61K 31/14; A61K 31/40
[52] U.S. Cl. ........................ 260/326.82; 260/326.85; 260/567.6 P
[58] Field of Search ..................... 260/326.85, 326.82, 260/567.6 P

[56] References Cited

U.S. PATENT DOCUMENTS

| | | | |
|---|---|---|---|
| 2,623,902 | 12/1952 | Crossley | 260/567.6 P |
| 2,760,978 | 8/1956 | Huebner | 260/567.6 P |

FOREIGN PATENT DOCUMENTS

| | | | |
|---|---|---|---|
| 741112 | 11/1955 | United Kingdom | 260/567.6 P |
| 991898 | 5/1965 | United Kingdom | 260/570 |

OTHER PUBLICATIONS

Khromor-Borisov, et al., (II) Pharmacological Reviews, 18, No. 3, pp. 1051–1090, (1966).
Van Allan, Chemical Abstracts, vol. 52, 1992f, (1956).
Price et al., J. Am. Chem. Soc., vol. 66, 632–633, (1944).
Kharkevitch et al., "The Pharmacology of Curariform Remedies", Meditsyna, Moscow, (1969), pp. 70–71 & pp. 125–128.
Matrka, Chemical Abstracts, vol. 55, 16473(b), (1961).
Khromov-Borisov et al., Chemical Abstracts, vol. 72, 21,452a, (1970).
Tomita et al., Chemical Abstracts, vol. 48, 6984b, (1953).
Fieser et al., Reagents for Organic Synthesis John Wiley & Sons, N.Y., (1967), pp. 440–441.
Issekutz, Arch. exper. Path. u. Pharmakol. Bd. 245, pp. 283–285, 297, (1952).
Krasovitskii et al., Chem. Abstracts, vol. 56, 3597a, (1962).
Matrka et al., Chem. Abstracts, vol. 60, 5368f, (1964).

*Primary Examiner*—Donald G. Daus
*Assistant Examiner*—Diana G. Rivers
*Attorney, Agent, or Firm*—Haseltine, Lake & Waters

[57] ABSTRACT p,p"-bis-Quaternary ammonium salts of n-terphenyl are characterized by the following formula

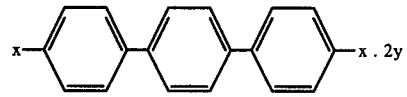

where x = N(R)$_2$R'
x = $\overset{+}{N}$(CH$_2$)$_4$R'  where R and R' = alkyl of from 1 to 3 carbon atoms
y = C$_6$H$_5$SO$_3$, Hal Said substances are prepared by a method consisting in reduction of p,p"-dinitro-p-terphenyl, alkylation of the resulting p,p"-diamino-p-terphenyl, and subsequent quaternization with alkyl esters of benzenesulphonic acid.

Said salts are nondepolarizing muscle relaxants possessing high potency and selectivity of action and can be used in medicine to block the neuromuscular conduction in surgical operations.

22 Claims, No Drawings p,p"BIS-QUATERNARY AMMONIUM SALTS OF p-TERPHENYL AND METHOD OF PREPARING SAME

This invention relates to organic synthesis and more particularly it relates to p,p"-bis-quaternary ammonium salts of p-terphenyl and a method of preparing same.

p,p"-bis-Quaternary ammonium salts of n-terphenyl are entirely new substances that have not been described in literature so far.

According to the invention, p,p"-bis-quaternary ammonium salts of p-terphenyl are characterized by the general formula

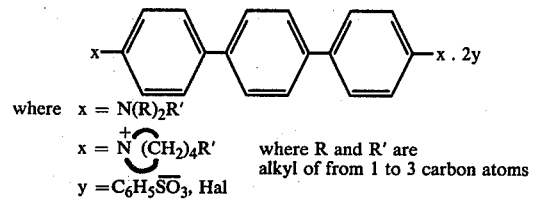

where  $x = N(R)_2R'$
$x = \overset{+}{N}(CH_2)_4R'$   where R and R' are alkyl of from 1 to 3 carbon atoms
$y = C_6H_5\overline{SO}_3$, Hal Representatives of these salts are p,p"-bis-trimethyl-ammonium-p-terphenyl dibenzenesulphonate having the formula

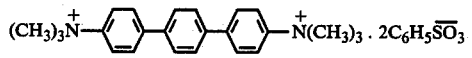

p,p"-bis-diethylmethylammonium-p-terphenyl dibenzenesulphonate having the formula

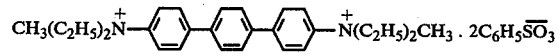

p,p"-bis-triethylammonium-p-terphenyl dibenzenesulphonate having the formula

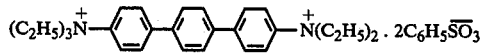

p,p"-bis-triethylammonium-p-terphenyl dibromide having the formula

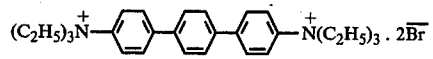

p,p"-bis dispropylmethylammonium-p-terphenyl dibenzenesulphonate having the formula

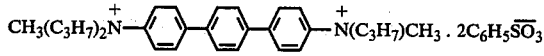

p,p"-bis-(N-methylpyrrolidinium)-p-terphenyl dibenzenesulphonate having the formula

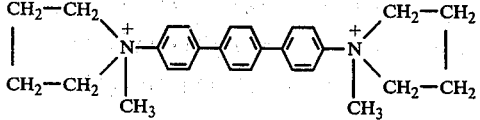

p,p"-bis-(N-ethylpyrrolidium)-p-terphenyl dibenzenesulphonate having the formula

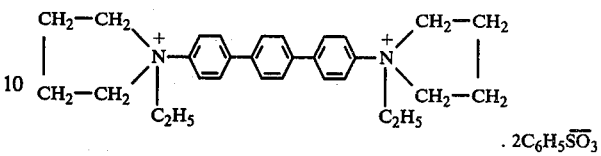

All the above-named substances are non-depolarizing muscle relaxants possessing high potency and selectivity of their action and can be used in medicine to block neuromuscular conduction in surgical operations.

In experiments on animals, the nervomuscular blocking activity of these substances proved to be close to or much higher than that of the known muscle relaxant of the same type, d-tubocurarin (Burroughs Wellcome Co. London).

At the same time, in contrast to the known non-depolarizing muscle relaxants d-tubocurarin and pyrolaxon (gallamin, flaxedil), all the above substances do not affect blood pressure since they do not produce histamine, or block the ganglia of the vegatative nervous system. Pyrolaxon is known to block the ganglia of the nervus vagus and to produce tachycardia. Relaxation of muscles produced by d-tubocurarin is associated with a fall in the arterial pressure because (in the blocking dose) it produces histamine from tissues and also blocks condition in the sympathic ganglia. Furthermore, in conditions of artificial lung ventilation, all the above p,p"-bis-quaternary ammonium salts of p-terphenyl, are non-toxic. Experimental animals tolerate dozens and hundreds of blocking doses of these substances, whereas even 5 to 10 doses of d-tubocurarin kill them. For example, cats tolerate 200 blocking doses of p,p"-bis-triethylammonium-p-terphenyl dibenzenesulphonate and dibromide, and only one out of three cats perished from a 1000-fold dose of these preparations. Death resulted from a fatal reduction in arterial pressure and cessation of heart activity.

It is known that preference in clinics is given to nondepolarizing muscle relaxants (compared with depolarizing preparations). This is firstly because the blocking action of nondepolarizing relaxants can be easily removed with anticholinesterase substances (proserin, nivalin), and secondly because they do not increase concentration of potassium in blood that otherwise produces grave complications in cardiovascular patients (with depolarizing muscle relaxants).

All the above substances are non-depolarizing muscle relaxants and their effect can be readily removed with inhibitors of cholinesterase. Moreover, they have higher specificity compared with d-tubocurarin. For example, in experiments on cats, proserin given in a dose of 0.1 mg/kg intravenously quickly and completely removes the action of five blocking doses of dibenzenesulphonate and dibromide of p,p"-bis-triethylamino-p-terphenyl and only three doses of d-tubocurarin.

Using the proposed substances in clinics as muscle relaxants ensures safe and controlled relaxation of muscles.

The neuromuscular blocking activity of the proposed substances is illustrated by way of comparison thereof with that of d-tubocurarin in the Table that follows. (BD and HDD stand for the block dose and head-drop dose respectively).

Table 1

$$x-\phenyl-\phenyl-\phenyl-x \cdot 2y$$

| x | y | CATS BD, MKW/kg | action | RABBITS HDD, MKM/kg |
|---|---|---|---|---|
| 1 | 2 | 3 | 4 | 5 |
| $\overset{+}{N}(CH_3)_3$ | $C_6H_5\overline{SO_3}$ | 0.3±0.04 | mixed | 0.25±0.05 |
| $\overset{+}{N}(C_2H_5)_2CH_3$ | $C_6H_5\overline{SO_3}$ | 0.5±0.09 | nondepolar | 0.12±0.02 |
| $\overset{+}{N}(C_2H_5)CH_3$ | $C_6H_5\overline{SO_3}$ | 0.08±0.002 | nondepolar | 0.022±0.001 |
| $\overset{+}{N}(C_2H_5)_3$ | $\overline{Br}$ | 0.08±0.002 | nondepolar | 0.022±0.001 |
| $\overset{+}{N}(C_3H_7)_2CH_3$ | $C_6H_5\overline{SO_3}$ | 0.5±0.1 | nondepolar | 0.1±0.03 |
| $\overset{+}{N}(CH_2)_4CH_3$ | $C_6H_5\overline{SO_3}$ | 1.0±0.2 | nondepolar | 0.3±0.06 |
| $\overset{+}{N}(CH_2)_4C_2H_5$ | $C_6H_5\overline{SO_3}$ | 0.5±0.08 | nondepolar | 0.14±0.04 |
| d-Tubocurarin | | 0.5±0.02 | nondepolar | 0.18±0.06 |

The Table shows that the highest blocking activity is observed in dibenzenesulphonate and dibromide of p,p''-bis-triethylammonium-p-terphenyl. The muscle paralytic activity of these compounds 6 to 8 times exceeds that of d-tubocurarin.

Unlike d-tubocurarin, the proposed substances do not produce histamine, they do not block the ganglia of the vegetative nervous system, and do not therefore affect the blood pressure. In experiments on cats and rabbits, only a transient and weak depressive effect is produced with a ten-fold dose of these substances. At the same time, a manifest reduction in the arterial pressure is observed with the administration of a myoparalytic dose of d-tubocurarin.

As has already been said, in conditions of artificial lung ventilation, these compounds are nontoxic. They also posses higher specificity of their action as compared with d-tubocurarin. For example, a dose of d-tubocurarin that blocks the neuromuscular condition, also blocks the upper cervical ganglion of cat. Dibenzenesulphonate and dibromide of p,p''-trie-thylaluminium-p-terphenyl produces only a weak ganglio-blocking effect when given in a dose ten times exceeding that producing neuromuscular block.

Cholinesterase inhibitors remove the blocking action of these preparations easier than the action of d-tubocurarin.

In experiments on decerebrated cats the action of these compounds did not enhance the action of fluorothane on the blood pressure, whereas d-tubocurarin intensifies the action of fluorothane (halothane) on the heart and their combined action is therefore considered dangerous due to possible cardiovuscular collapse.

Experimental comparison of these preparations with the known nondepolarizing muscle relaxant pancuronium (Organon Inc. W. Orange, N.Y. 07052) has shown that the proposed preparations posses certain advantages.

As has already been mentioned, the proposed substances given in doses much exceeding their myoparalytic doses, do no affect arterial pressure. The disadvantage of pancuronium is that it can accelerate the pulse rate and increase arterial pressure, which intensifies hemorrhage in surgical operations.

The antagonistic action of proserpin in experiments with the proposed preparation on cats was more manifest compared with the known preparation pancuronium. With 4 to 5-fold doses of pancuronium, the muscular contractility began restoring no sooner than in ten minutes after injection of proserin in a dose of 0.1 mg/kg intravenously. In the same conditions, proserpin, given in the same dose, completely removed the blocking effect of the proposed substances given in doses several times exceeding the myoparalytic dose. Even with five-fold doses of these preparations, the muscle contractility began restoring within five minutes after a single injection of proserpin in a dose of 0.1 mg/kg.

This indicates that using the proposed preparations in clinic ensures safe and controlled relaxation of muscles (compared with d-tubocurarin and pancuronium).

The advantage of the proposed substances is simplicity of their synthesis out of readily available and inexpensive starting materials, reagents, and solvents.

According to the invention, p,p''-bis-quaternary ammonium-salts of p-terphenyl are synthesized as follows.

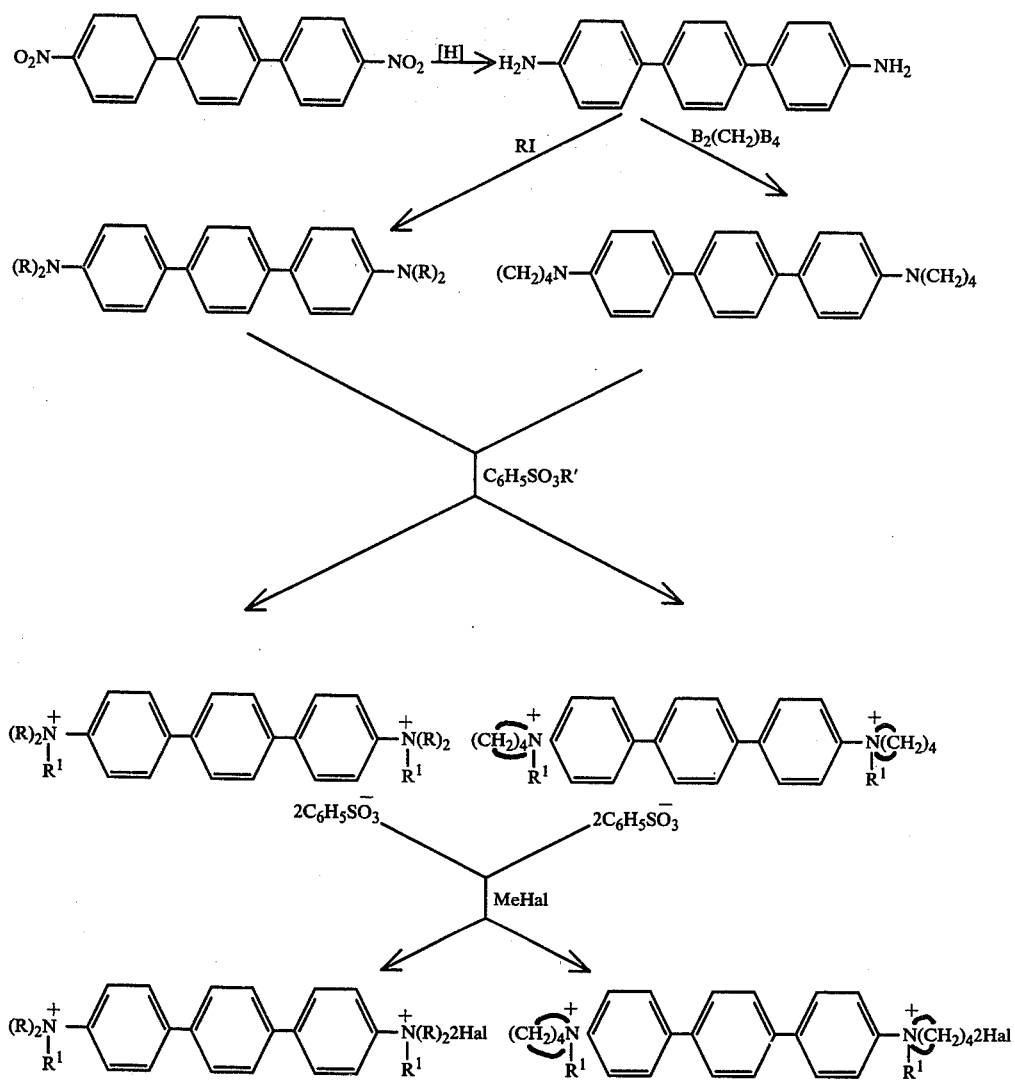

where R and R' are alkyl of from 1 to 3 carbon atoms, and Me and Na, K.

The method of preparing p,p″-bis-quaternary ammonium salts of p-terphenyl consists in reduction of p,p″-dinitro-p-terphenyl to p,p″-diamino-p-terphanyl; alkylation of p,p″-diamino-p-terphenyl to p,p″-bis(tertiary-amino)-p-terphenyls with alkyl iodides or tetramethylene dibromide; quaternization of p,p″-bis-(tertiary-amino)-p-terphenyls with alkyl esters of benzenesulphonic acid to p,p″-bis(quaternary-ammonium)-p-terphenyl dibenzenesulphonates; whenever halides of p,p″-bis-(quaternary-ammonium)-p-terphenyls are required, the process comprises also replacement of the anion of benzenesulphonic acid in p,p″-bis(quaternary-ammonium)-p-terphenyl dibenzenesulphonates with halide ion by treating with a mineral halide.

The starting substance, n,n″dinitro-n-terphenyl, is a readily available substance by nitration of p-terphenyl with fuming nitric acid.

p,p″-Dinitro-p-terphenyl can be reduced for example, with catalytic hydrogenation in an autoclave for 2 to 3 hours.

Moreover, it is possible to reduce p,p″-dinitro-p-terphenyl by stannous chloride solution in concentrated hydrochloric acid for three hours.

But a faster and easier way to reduce p,p″-dinitro-p-terphenyl consists in using hydrazine hydrate in the presence of Raney nickel in an inert organic solvent, e.g., ethylene glycol, with heating. This takes only a few minutes and the yield of p,p″-diamino-p-terphenyl is quantitative.

p,p″-Diamino-p-terphenyl can be alkylated with various agents, e.g. alkyl iodides, in the presence of an agent binding iodine, in an inert organic solvent with heating.

p,p″-bis-(tertiary-amino)-p-terphenyls are quaternized in solution with alkyl esters of benzenesulphonic acid with heating.

Whenever halides of p,p″-bis(quaternary-ammonium)-p-terphenyls are required, they are prepared by the action of a mineral halide on an aqueous solution of the corresponding p,p″-bis(quaternary-ammonium)-p-terphenyl dibenzenesulphonate.

Diiodides of p,p″-bis(quaternary-ammonium)-p-terphenyl are sparingly soluble in water at room temperature and are of little interest for pharmacological purposes.

The proposed method can be realized as follows.

The starting p,p″-dinitro-p-terphenyl is placed in a flask provided with a reflux condenser, thermometer, a stirrer and a dropping funnel. Ethylene glycol and a hydrogenation catalyst are added and the contents are heated on an oil bath. When the temperature of the suspension is 165° C, hydrazine hydrate is added with the mixture being intensively stirred to avoid strong foaming. The reaction is continued for a few minutes, all the components are dissolved, the solution is heated for another few minutes with activated carbon at a temperature of 165 to 180° C. The reaction mixture is filtered; the precipitate that falls out on cooling the filtrate is separated on a filter, washed with absolute alcohol and dried. p,p''-Diamino-p-terphenyl obtained by this method does not require additional purification. The yield is quantitative.

p,p''-Diamino-p-terphenyl is placed in a flask provided with a reflux condenser and a stirrer; water, an inert organic solvent, calcium carbonate and alkyl iodide or tetramethylene dibromide are added. The reaction mixture is heated with stirring for 2 to 4 hours. In the process of heating, p,p''-bis-(tertiary-amino)-p-terphenyl begins precipitating. It is separated on a filter after cooling the reaction mixture.

The precipitate is crystallized from an organic solvent. The yield of p,p''-bis-(tertiary-amino)-p-terphenyls is 70 to 96%.

p,p''-bis(Tertiary-amino)-p-terphenyl is heated in a flask or in a beaker for a few minutes, or for an hour, in solution of alkyl ester of benzenesulphonate at a temperature of 120 to 200° C. By the end of heating the solution becomes thick. The mass is cooled and treated with absolute diethyl ether or anhydrous acetone, and the obtained precipitate is crystallized from acetone and water. The yield of p,p''-bis-(quaternary-ammonium)-p-terphenyl dibenzenesulphonates is 70 to 80%.

In order to prepare halides of p,p''-bis(quaternary-ammonium)-p-terphenyls, p,p''-bis(quaternary-ammonium)-p-terphenyl dibenzene sulphonate is placed in a flask provided with a stirrer, dissolved in water, and a 5-fold excess of the appropriate mineral halide is added in portions with slightly heating the mixture. The solution is allowed to stand overnight at room temperature and then cooled. The precipitate is separated on a filter, and crystallized from aqueous solution of acetone. The yield of p,p''-bis-(quaternary-ammonium)-p-terphenyl halide is quantitative.

As becomes clear from the description the proposed method for preparing p,p''-bis-quaternary-ammonium salts of p-terphenyl consists of three stages, that require little time and give good yields. The synthesis requires widely known and readily available reagents and solvents, purification of the end product is simple. This method can be easily realized on an industrial scale and is commercially advantageous.

For a better understanding of the invention, the following examples of its practical embodiment are given by way of illustration.

EXAMPLE 1

Preparing p,p''-bis-trimethylammonium-p-terphenyl dibenzenesulphonate (a) Reduction of p,p''-dinitro-p-terphenyl A three-neck flask of 1-litre capacity, provided with a reflux condenser, a stirrer, a thermometer, and a dropping funnel, is loaded with 10 g of suspension of p,p''-dinitro-p-terphenyl in 500 ml of ethylene glycol, then 5 ml of freshly prepared Raney nickel are added, and finally, with stirring and heating (the temperature in the flask should be 165 to 170° C) added carefully in drops are 15 ml of a 99 percent solution of hydrazine hydrate (intense foaming should be avoided).

The components of the mixture are dissolved in a few minutes and activated carbon is then added. In 10 to 15 minutes, the hot solution is filtered and the filtrate cooled.

The precipitate is washed on a filter with alcohol and dried. The yield of p,p''-diamino-p-terphenyl is 8.1 g (quantitative). The product melts at 240° C.

(b) Alkylation of p,p''-diamino-p-terphenyl with methyl iodide.

A 250 ml flask provided with a reflux condenser and a stirrer is loaded with 1.7 g of p,p''-diamino-p-terphenyl, 2.2 g of calcium carbonate, 75 ml of ethylene glycol, 8 ml of water and 5 ml of methyl iodide.

During stirring, the suspension is heated at 70° C, and as methyl iodide enters into reaction, the temperature is further raised to 100–120° C. Heating is continued for 5 hours. The heated solution is filtered and the filtrate is cooled. The precipitate (2g) which is brick-coloured and has a decomposition temperature of about 250° C, is essentially a mixture of p,p''-bis--dimethylamino-p-terphenyl and p,p''-bis trimethylammonium-p-terphenyl diiodide.

(c) Quaternization with methyl benzenesulphonate

A 100-ml flask is loaded with 2 g of the above mixture of p,p''-bis-dimethylamino-p-terphenyl and p,p''-bis-trimethylammonium-p-terphenyl diiodide and heated with 30 ml of methyl benzenesulphonate for two hours, first at a temperature of 100° C, then at 120° C. By the end of heating, the solution thickens. The mass is cooled, treated with absolute diethyl ether, and filtered.

The beige precipitate (2.5 g, 80 percent) is crystallized from 50 ml of water with activated carbon.

The obtained p,p''-bis-trimethylammonium-p-terphenyl dibenzenesulphonate is greenish. The m.p. is above 300° C. The product is dried in vacuum and kept in the dark.

Found, in percent: C 65.50, 65.57; H 6.49, 6.41; S 9.68, 9.61; $C_{36}H_{40}N_2O_6S_2$. Calculated, in percent: C 65.43, H 6.10, S 9.68.

EXAMPLE 2

Preparation of p,p''-diethylammonium-p-terphenyl dibenzenesulphonate (a) Reduction of p,p''9dinitro-p-terphenyl is performed as in Example 1.

(b) Alkylation of p,p''-diamino-p-terphenyl with ethyl iodide.

A 250-ml flask provided with a reflux condenser and stirrer, is loaded with 8 g of p,p''-diamino-p-terphenyl, 10 g of calcium carbonate, 100 ml of dimethylformamide, 10 ml of water and 23 ml of ethyl iodide, and the mixture is heated on a bath at a temperature of 120 to 130° C. In a few minutes, the components are dissolved, and the precipitation process begins immediately. Heating is continued for another two hours with energetically stirring the mixture, which is then cooled. The precipitate is separated on a filter, crystallized from 100 ml of dimethyl formamide, and 7.65 g of pale beige p,p''-bis-diethylamino-p-terphenyl are obtained. (The yield is 70 percent). The m.p. is 198° C.

Found, in percent: C 83.30, 83.42; H 8.68, 8.61; N 7.63, 7.61 $C_{26}H_{32}N_2$. Calculated, in percent: C 83.82; H 8.65, N 7.52.

(c) Quaternization of p,p''-bis-diethylamino-p-terphenyl with methyl benzenesulphonate.

A 50-ml flask is loaded with 1 g of p,p''-bis-diethylamino-p-terphenyl and heated with 5 ml of methyl benzenesulfonate at a temperature of 120° C for an hour.

The resulting solution thickens and crystals precipitate on cooling. The solid mass is crystallized on cooling, treated with absolute diethyl ether, and filtered.

The pale beige precipitate is crystallized from 30 ml of aqueous acetone (acetone to water ratio 10:1) with activated carbon.

The yield of p,p''-bis-diethylmethylammonium-p-terphenyl is 1.5 g, which is 80 percent. The product is white but becomes slightly green on exposure to air. The decomposition point is 270.5° C. The product is dried in vacuum and kept in the dark.

Found, in percent: C 67.35, 67.10; H 6.88, 7.05; S 9.16, 9.15; N 3.78, 3.77. $C_{40}H_{48}N_2O_6S_2$. Calculated, in percent: C 67.02, H 6.75, S 8.92, N 3.90.

EXAMPLE 3

Preparation of p,p''-bis-triethylammonium-p-terphenyl dibenzenesulphonate (a) Reduction of p,p''-dinitro-p-terphenyl is done as in Example 1.
(b) Alkylation of p,p''-diamino-p-terphenyl with ethyl iodide is done as in Example 2.
(c) Quaternization of p,p''-bis-diethylamino-p-terphenyl with ethyl benzenesulphonate.

A 100-ml flask is loaded with 7.5 g of p,p''-diethylamino-p-terphenyl and heated for an hour with 20 ml of ethyl benzenesulphonate at a temperature of the bath of 140° C. The components are dissolved within the first thirty minutes and by the end of the heating process crystallization occurs. The mixture is cooled, processed with absolute diethyl ether, and filtered.

The pale beige precipitate is crystallized from 100 ml of aqueous acetone (acetone to water ratio 10:1) with activated carbon. The yield of p,p''-bis-triethylammonium-p-terphenyl dibenzenesulphonate is 10 g (70 percent). The product is white but becomes greenish in air. The decomposition point, 228 to 229° C. The product is dried in vacuum and kept in the dark.

Found, in percent: C 67.97, 68.22, H 7.76, 7.66, S 8.75, 8.55, N 3.80, 3.90. $C_{42}H_{52}N_2O_6S_2$. Calculated, in percent: C 67.72, H 7.04, S 8.59, N 3.76.

EXAMPLE 4

Preparation of p,p''-bis-triethylammonium-p-terphenyl (a) Reduction of p,p''-dinitro-p-terphenyl is done as in Example 1.
(b) Alkylation of p,p''-diamino-p-terphenyl with ethyl iodide is done as in Example 2.
(c) Quaternization of p,p''-bis-diethylamino-p-terphenyl with ethyl benzenesulphonate is done as in Example 3.
(d) Preparation of p,p''-bis-triethylammonium-p-terphenyl dibromide from n,n''-triethylammonium-n-terphenyl.

A 250-ml flask provided with a stirrer, is loaded with 4/5 g of p,p''-bis-triethylammonium-p-terphenyl dibenzenesulphonate in 50 ml of water and 7 g of sodium bromide are added with stirring and heating. The solution is allowed to stand for 12 hours at room temperature and then cooled.

The precipitate is separated on a filter, then crystallized from 100 ml of acetone and water (10:1).

The yield of p,p''-bis-triethylammonium-p-terphenyl is 4.2 g (95 per cent). This is a white product slightly green when exposed to air; decomposed at 195 to 197° C. The product is dried in vacuum and kept in the dark.

Found, in per cent: C 54.25, 54.63; H 7.60, 7.70, Br 23.90 24.20, N 4.29, 4.16. $C_{30}H_{42}Br_2N_2 \cdot 4h_2O$. Calculated, in per cent: C 54.38, H 7.60, Br 24.12, N 4.23.

EXAMPLE 5

Preparation of p,p''-bis-dipropylmethylammonium-p-terphenyl dibenzenesulphonate.

(a) Reduction of p,p''-dinitro-p-terphenyl is done as in Example 1.
(b) Alkylation of p,p''-diamino-p-terphenyl with propyl iodide.

A 50-ml flask provided with a reflux condenser and a stirrer, is loaded with 2.1 g of p,p''-diamino-p-terphenyl, 2 g of calcium carbonate, 25 ml of dimethyl formamide, 2.5 ml of water and 7 ml of propyl iodide, and the mixture is heated for two hours at a temperature of 100 to 120° C on a bath. The reaction mixture is cooled, the precipitate is filtered, and crystallized from 30 ml of dimethyl formamide and water (5:1) with activated carbon.

The yield of p,p''-bis-dipropylamino-p-terphenyl is 2.45 g (70 per cent). This is a white product melting at 115 to 116° C.

Found, in per cent: C 84.03, 84.49, H 9.71, 9.57, N 7.03, 6.98. $C_{30}H_{40}N_2$. Calculated, in per cent: C 84.06, H 9.40, 6.53.

(c) Quaternization of p,p''-bis-dipropylamino-p-terphenyl with methyl benzenesulphonate.

A 50-ml flask is loaded with 1 g of p,p''-bis-dipropylamino-p-terphenyl and heated for 15 minutes with 3 ml of methyl benzenesulphonate at a temperature of the bath of 120° C. In seven minutes, the solution begins crystallizing. The mixture is cooled and treated with anhydrous acetone, the precipitate is filtered and crystallized from 30 ml of acetone and water (10:1) with activated carbon.

The yield of p,p''-bis-dipropylmethylammonium-p-terphenyl dibenzenesulphonate is 1.45 g (80 per cent). The product is a white substance that becomes slightly green on exposure to air. The decomposition point is 245° C. The product is dried in vacuum and kept in the dark.

Found, in per cent: C 66.39, 66.37, H 7.19, 7.43, N 3.59, 3.33, S 8.24, 8.19. $C_{44}H_{56}N_2O_6S_2 \cdot H_2O$. Calculated, in per cent: C 66.81, H 7.39, N 3.54, S 8.28.

EXAMPLE 6

Preparation of p,p''-bis-(N-methylpyrrolidinium)-p-terphenyl dibenzenesulphonate (a) Reduction of p,p''-dinitro-p-terphenyl is done as in Example 1.
(b) Alkylation of p,p''-diamino-p-terphenyl with tetramethylene dibromide.

A 250-ml flask provided with a reflux condenser and a stirrer is loaded with 5.2 g of p,p''-diamino-p-terphenyl, 4.5 g of calcium carbonate, 50 ml of dimethyl formamide, 5 ml of water and 8.6 g of tetramethylene dibromide, and heated for four hours on a bath at a temperature of 110 to 125° C. The cooled suspension is filtered to separate 7.1 g (96 per cent) of a precipitate of sandy colour. The precipitate is only slightly soluble in organic solvents and cannot therefore be additionally purified. The melting point is about 310° C.

An analytical sample of p,p"-bis(N-pyrrolidinium)-p-terphenyl is prepared by crystallization from a large quantity of dimethyl formamide.

Found, in per cent: C 84.47, 84.61, H 7.42, 7.59, N 7.34, 7.20. $C_{26}H_{28}N_2$. Calculated, in per cent: C 84.74, H 7.66, N 7.60.

Quaternization of p,p"-bis-(B-pyrrolidinium)-p-terphenyl is done with methyl benzenesulphonate.

A 50-ml flask is loaded with 1 g of p,p"-bis(N-pyrolidinyl)-p-terphenyl, 10 ml of methyl benzenesulphonate are added and the components are heated for fifteen minutes on a bath at a temperature of 200° C. The mixture is then immediately cooled and treated with absolute ether, the precipitate is separated and crystallized from 30 ml of acetone and water (10:1) with activated carbon.

The yield of p,p"-bis-(N-methylpyrrolidinium)-p-terphenyl dibenzenesulphonate is 1.45 g (76 per cent). The product is a white substance that becomes green on exposure to air. The decomposition point is 273 to 274° C. The product is dried in vacuum and kept in the dark.

Found, in per cent: C 64.74, 64.45; H 6.91, 6.66, N 3.94 3.77, S 8.89, 9.03. $C_{40}H_{44}N_2O_6S_2 \cdot H_2O$. Calculated, in per cent: C 64.15, H 6.46, N 3.74, S 8.55.

EXAMPLE 7

Preparation of p,p"-bis(N-ethylpyrrolidinium)-p-terphenyl dibenzenesulphonate (a) Reduction of p,p"-dinitro-p-terphenyl is done as in Example 1.
(b) Alkylation of p,p"-diamino-p-terphenyl with tetramethylene dibromide is done as in Example 6.
(c) Quaternization of p,p"-bis(N-pyrrolidinyl)-p-terphenyl with ethyl benzenesulphonate.

A 50-ml flask is loaded with 1 g of p,p"-bis-(N-pyrolinidyl)-p-terphenyl and heated with 6 ml of ethyl benzenesulphonate for ten minutes on a bath at a temperature of 200° C. The reaction mixture is then cooled and treated with anhydrous acetone. The precipitate is filtered and crystallized from 30 ml of acetone and water (10:1) with activated carbon. The yield of p,p"-bis-(N-ethylpyrrolidinium)-p-terphenyl dibenzenesulphonate is 1.6 g (80 per cent). The product is a white substance that becomes green on exposure to air. The decomposition point is 277° C.

The product is dried in vacuum and kept in the dark.
Found, in per cent: C 66.50, 66.55; H 6.85, 6.70, N 3.33, 3.65, S 8.43, 8.49. $C_{42}H_{48}N_2O_6S_2 \cdot H_2O$. Calculated, in per cent: C 66.47, H 6.46, N 3.69, S 8.43.

What is claimed is:
1. p,p"-bis-Quaternary ammonium salts of p-terphenyl of the formula

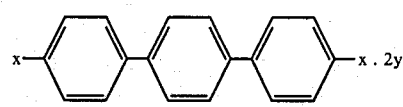

where $x = \overset{+}{N}(R)_2R'$
$x = \overset{+}{N}(CH_2)_4R'$    R and R' are alkyl of from 1 to 3 carbon atoms
$y = C_6H_5\overline{SO_3}$, Hal.

2. p,p"-bis-Trimethylammonium-p-terphenyl dibenzenesulphonate according to claim 1, of the formula

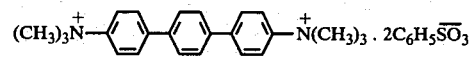

3. p,p"-bis-Diethylmethylammonium-p-terphenyl dibenzenesulphonate according to claim 1, of the formula

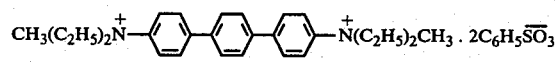

4. p,p"-bis-Triethylammonium-p-terphenyl dibenzenesulphonate, according to claim 1, of the formula

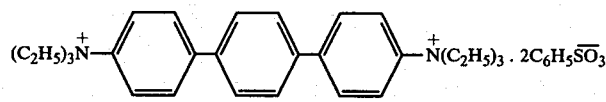

5. p,p"-bis-Triethylammonnium-p-terphenyl dibromide according to claim 1, of the formula

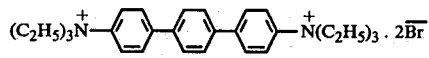

6. p,p"-Dipropylmethylammonium-p-terphenyl dibenzenesulphonate according to claim 1, of the formula

7. p,p"-bis-(N-methylpyrrolidinium)-p-terphenyl dibenzenesulphonate according to claim 1, of the formula

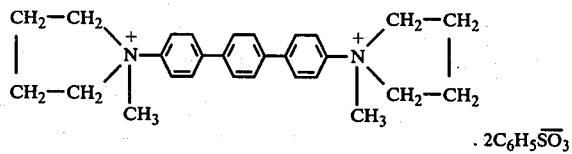

8. p,p"-bis(N-ethylpyrrolidinium)-p-terphenyl dibenzenesulphonate according to claim 1, of the formula

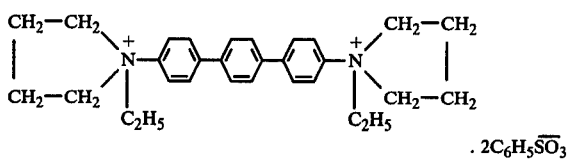

. 2C₆H₅S̄O₃

9. A method for preparing p,p''-bis-quaternary ammonium salts of p-terphenyl according to claim 1, consisting in reduction of p,p''-dinitro-p-terphenyl to p,p''-diamino-p-terphenyl with hydrazine hydrate in the presence of Raney nickel in ethylene glycol at between 165° and 180° C; alkylation of p,p''-diamino-p-terphenyl to p,p''-bis(tertiary-amino)-p-terphenyls with alkyl iodides or tetramethylene dibromide; quaternization of p,p''-bis(tertiary-amino)-p-terphenyl with alkyl esters of benzenesulphonic acid to form p,p''-bis(quaternary-ammonium)-p-terphenyl benzenesulphonates.

10. A method according to claim 9, in which halides of said substances are obtained by treating p,p''-bis(-quaternary-ammonium)-p-terphenyl dibenzenesulphonates with inorganic halide.

11. A method according to claim 9, in which alkylation of p,p''-diamino-p-terphenyl is done with alkyl iodides in a medium of an inert organic solvent with heating.

12. A method according to claim 9, in which alkylation of p,p''-diamino-p-terphenyl is effected in the presence of an agent binding halide.

13. A method according in claim 9, in which alkylation is effected in an inert organic solvent containing water.

14. A method according to claim 11, in which alkylation is effected with methyl iodide in methyl alcohol and water at a temperature of 70 to 120° C.

15. A method according to claim 11, in which alkylation is effected with ethyl iodide in dimethyl formamide and water at a temperature of 120 to 130° C.

16. A method according to claim 11, in which alkylation is effected with propyl iodide in dimethyl formamide with water at a temperature of 100 to 120° C.

17. A method according to claim 9, in which alkylation is effected with tetramethylene dibromide in dimethyl formamide with water at a temperature of 110 to 125° C.

18. A method according to claim 9, in which alkylation is effected with heating for 2 to 5 hours.

19. A method according to claim 9, in which quaternization of p,p''-bis(tertiary-amino)-p-terphenyls is effected with alkyl esters of benzenesulphonic acid with heating.

20. A method according to claim 19, in which quaternization is effected in a solution of methyl benzenesulphonate at a temperature of 120 to 200° C.

21. A method according to claim 19, in which quaternization is effected in a solution of ethyl benzenesulphonate at a temperature of 140 to 200° C.

22. A method according to claim 19, in which quaternization is effected with heating for a period of time from ten minutes to two hours.

* * * * *